United States Patent [19]

Singh et al.

[11] Patent Number: 5,089,388
[45] Date of Patent: Feb. 18, 1992

[54] ANTIBODIES FOR SALICYLATE AND THEIR PREPARATION

[75] Inventors: Prithipal Singh, Sunnyvale; Michael Prisbylla, Richmond, both of Calif.

[73] Assignee: Syntex (U.S.A.) Inc., Palo Alto, Calif.

[21] Appl. No.: 833,659

[22] Filed: Feb. 21, 1986

Related U.S. Application Data

[63] Continuation of Ser. No. 486,575, Apr. 19, 1983, abandoned.

[51] Int. Cl.$^5$ .............. C12Q 1/00; C12Q 1/32; G01N 33/532; G01N 33/557
[52] U.S. Cl. .............. 435/7.6; 435/7.9; 435/26; 435/188; 435/190; 436/517; 436/544; 436/546; 436/815
[58] Field of Search .............. 435/7, 26, 188, 190, 435/7.6, 7.9; 436/517, 536, 544, 545, 546, 815

[56] References Cited

U.S. PATENT DOCUMENTS

| | | | |
|---|---|---|---|
| 3,817,837 | 6/1974 | Rubenstein et al. | 435/7 |
| 3,875,011 | 4/1975 | Rubenstein et al. | 435/188 |
| 4,331,590 | 5/1982 | Bocuslaski et al. | 435/188 X |
| 4,360,592 | 11/1982 | Weltman | 435/7 |
| 4,420,568 | 12/1983 | Wang et al. | 436/817 X |
| 4,443,365 | 4/1984 | Sunahara et al. | 435/7 X |
| 4,476,229 | 10/1984 | Fino et al. | 436/537 X |

OTHER PUBLICATIONS

Thomas et al, J. Pharm. Pharmac., vol. 25, (1973), pp. 201–204.
Rance et al, J. Pharm. Pharmac., vol. 27, (1975), pp. 425–429.
Fraser, Therapeutic Drug Monitoring, vol. 5, No. 3, (1983), pp. 331–334.
Grant & Hackh's Chemical Dictionary, 5th edition, (1987), pp. 55 and 515.

*Primary Examiner*—Jeffrey Edwin Russel
*Attorney, Agent, or Firm*—Theodore J. Leitereg; Carole F. Barrett; Gerald F. Swiss

[57] ABSTRACT

Conjugates of salicylic acid and certain poly(amino acids), which are either antigenic or enzymes, are provided. Antibodies raised against the antigenic poly(amino acids) and the enzyme conjugates are used as reagents in immunoassays.

6 Claims, No Drawings

ANTIBODIES FOR SALICYLATE AND THEIR PREPARATION

This application is a continuation of Application Ser. No. 486,575, filed Apr. 19, 1983, now abandoned.

BACKGROUND OF THE INVENTION

1. Field of the Invention

Aspirin (acetylsalicylic acid) and certain closely related compounds are the most commonly used therapeutic drugs in the world. The drug has a very short half life after administration and is rapidly metabolized to salicylic acid (hereafter called salicylate). Although generally recognized as safe, plasma salicylate levels of 30mg/dl and above may be toxic, with levels exceeding 40mg/dl sometimes being fatal. Since therapeutic levels of aspirin for the treatment of rheumatoid arthritis are usually in the range from 20-30mg/dl, it is desirable to be able to monitor the dosage of aspirin in order to assure that the plasma salicylate levels are in an effective but safe range.

Heretofore, plasma salicylate monitoring has usually been accomplished by either colorimetric methods or by high pressure liquid chromatography. Each of these techniques can be difficult and time-consuming. It would therefore be desirable to provide the compounds necessary to perform immunoassays for the determination of salicylate in plasma.

2. Description of Prior Art

Antibodies to aspirin and related compounds have been described by Wicher, et al. (1968) *J. Immunol.* 101:342-348, and Hoffman and Campbell (1969) *J. Immunol.* 103:655-661. Singh et al., *Anal. Biochem.* (1980) 104:51-58 describe the use of a methyldithioacetic acid and bromoacetylglycine combination for linking gentamicin to glucose-6-phosphate dehydrogenase.

SUMMARY OF THE INVENTION

Salicylic acid derivatives are conjugated to proteins, such as antigens and enzymes. The antigens are used for production of antibodies to salicylates, which antibodies together with the enzyme conjugates are used as reagents in sensitive immunoassays for monitoring salicylate in serum.

DESCRIPTION OF THE SPECIFIC EMBODIMENT

The compounds of this invention are precursors for conjugation to polypeptides and the resulting polypeptide conjugates. These conjugates find use as immunogens for production of antibodies to salicyclic acid, (anti-(salicylic acid)) and where the polypeptide is an enzyme as a reagent in immunoassays, particularly homogeneous immunoassays.

For the most part, the compounds of this invention will have the following formula:

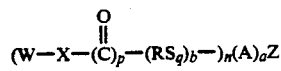

wherein:
W is 3-carboxy-4-hydroxyphenyl-1;
X is a bond or —NH—;
p is 0 or 1, being 1 when X is NH; atoms;
S is sulphur;
b is 0 or 1;
q is 0 or 1;
Z is H,—S—lower alkyl, —CO—lower alkyl or a poly(amino acid), where lower alkyl is of from 1 to 6, usually 1 to 3 carbon atoms, q being 1, when Z is S-lower alkyl or —CO—lower alkyl;
n is 1, when Z is other than a poly(amino acid), and 1 to the molecular weight of said poly(amino acid) divided by 500, usually 1,000, more usually 2,000, when Z is a poly(amino acid);
a is 0 up to n, being 0 when q is 0;
A is derived from a functionality capable of reacting with a thiol group and includes α-acetyl, N-α-acetylglycyl, and α-succinimidyl.

When X is a bond, a, p and q are 0 and b is 1, the compounds of this invention will have the following formula:

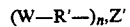

wherein:
R' is an aliphatic linking group having a chain of from 1 to 4 carbon atoms, usually being a branched or unbranched hydrocarbon aliphatic linking group; more usually being an alkylene linking group, such as methylene, polymethylene, ethylene, butylene and isobutylene; most commonly R' will have the formula $(CH_2)_m$ where m is from 1 to 4, usually 1 to 2, most often 1;
Z' is a poly(amino acid) which is antigenic or an enzyme; and
n' is from 1 to the molecular weight of Z' divided by 500, more usually divided by 1,000 and frequently divided by 1,500.

When Z' is an antigen, n' usually ranges from 1 to 500, typically from 10 to 100; and when Z' is an enzyme, n' usually ranges from 1 to 30, more usually from 2 to 20, normally being from about 2 to 16.

When b and q are 1, the compounds of this invention will have the following formula:

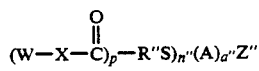

wherein:
R" is an aliphatic linking group having a chain of from 1 to 4 carbon atoms, having the same definition as R', except being preferably from 1 to 3 carbon atoms;
Z" is a poly(amino acid), either an antigen or enzyme of from about 10,000 to about 600,000 molecular weight or —S—lower alkyl or —CO—lower alkyl;
a" is equal to n";
n" is 1 when a" is 0 and Z" is S-lower alkyl and —CO—lower alkyl;
n" is 1 to the molecular weight of Z" divided by 1,000, usually divided by 2,000, more usually divided by 2,500; and
the remaining symbols have been defined previously.

The molecular weight of the poly(amino acids) will generally be at least about 5,000 and have no upper limit, normally being less than 10,000,000, and usually being not more than about 600,000. There will usually be different ranges depending on whether an antigen or an enzyme is invoived. With antigens, the range will be from about 5,000 to 10,000,000, usually from about 20,000 to 600,000, and more usually from about 25,000 to 250,000 molecular weight. -With enzymes, the range will be from about 10,000 to 600,000, and more usually from about 10,000 to 300,000 molecular weight. For both antigens and enzymes, there will usually be at least about 1 salicylate group per 200,000 molecular weight, more usually at least one per 50,000 molecular weight. In the case of intermediate molecular weight antigens (35,000 to 600,000), the number of salicylate groups will generally be from about 2 to 250, more usually from 10 to 100. With lower molecular weight antigens, (below 35,000), the number of salicylate groups will generally be in the range from about 2 to 10, usually in the range from 2 to 5.

Various protein types may be employed as the antigenic material. These types include albumins, serum proteins, e.g., globulins, ocular lens proteins, lipoproteins, and the like. Illustrative proteins include bovine serum albumin, keyhole limpet hemocyanin, egg ovalbumin, bovine gamma-globulin, and the like. Alternatively, synthetic poly(amino acids) may be prepared having sufficient available amino groups, e.g., lysines.

The enzymes can vary widely, depending on the ease of conjugation, turnover rate, and the physiological fluid in which the salicylate is to be measured. Primarily, the enzymes of choice, based on the I.U.B. classifications are: Class 1, Oxidoreductases and Class 3, hydrolases. Particularly in Class 1, the enzymes of interest are dehydrogenases of Class 1.1, more particularly, Sub-classes 1.1.1 and 1.1.99 and peroxidases in Class 1.11. Of the hydrolases, particularly class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Illustrative hydrolases include alkaline phosphatase, beta-galactosidase, beta-glucosidase and lysozyme.

Particularly preferred are those enzymes which employ nicotinamide adenine dinucleotide (AND), or its phosphate (NADP) as a cofactor, particularly the former, or the reduced forms thereof. Illustrative of these enzymes is glucose-6-phosphate dehydrogenase.

Depending on the nature of the salicylic acid, the immunogen and enzyme conjugate may be prepared in a variety of ways. Where an aldehyde is the functional group, e.g. X is a bond, b is 0, and the subject immunogen and enzyme conjugates can be prepared from 5-formylsalicylic acid by reductive amination with the desired poly(amino acid). Such reductive amination is described generally in Borch, et al. (1971) *J. Amer. Chem. Soc.* 93:2897, and Lane (1975) *J. Syn.* 135. Specific conjugation procedures are described in detail in the Examples hereinafter.

The thio derivatives can be obtained by forming the halide of an alcohol from the aldehyde in a derivative providing an extended chain, and substituting the halide with the appropriate thio compound. Alternatively, 5-aminosalicylic acid may be functionalized with an acyl group having the appropriate dithio substituent for the thio linkage the polypeptide will be functionalized with a convenient functional group, such as an active halogen, e.g. bromoacetyl or an active ethylene, e.g. maleimidyl.

By employing the procedures to be exemplified, the hydroxyl and carboxyl moieties present on the salicylates are retained during the conjugation procedures. These moieties, which provide for a distinction between closely similar compounds, are exposed and result in formation of antibodies having low or no cross-reactivity with structurally similar compounds.

The immunogen conjugates may be injected into a wide variety of vertebrates in accordance with conventional methods for the production of antibodies. Usually, the animals are bled periodically, with successive bleeds having improved titer and specificity, until reaching a plateau and then diminishing in their specificity and titer. The immunogen conjugates may be injected intramuscularly, intraperitoneally, subcutaneously, or the like. Usually, a vehicle is employed, such as complete or incomplete Freund's adjuvant.

The antibodies and enzyme reagents prepared in accordance with the subject invention find particular use in immunoassays for the determination of salicylates in biological specimens. A description of the method for carrying out a homogeneous enzyme immunoassay may be found in U.S. Pat. No. 3,817,837. The method involves combining the enzyme conjugate, the sample which contains the salicylates, and an antibody for salicylates and an aqueous buffered medium at temperatures in the range from about 10–50° C., usually from about 20–40° C.

The following examples are offered by way of illustration and not by way of limitation.

EXPERIMENTAL

Melting points were determined on a Thomas-Hoover capillary melting point apparatus and are uncorrected. H NMR spectra were determined on a Varian EM-390 spectrometer as solutions in the indicated solvents. Chemical shifts are reported in $\delta$ units from the internal reference, tetramethylsilane. Singlet, doublet, triplet, quartet, and multiplet are abbreviated as s, d, t, q, and m, respectively, and J stands for the coupling constant measured in hertz (Hz). Infrared spectra (IR) were recorded on a Perkin-Elmer 297 spectrophotometer as indicated. Analysis and mass spectra were performed by Stanford University, Palo Alto, Calif. Chromatography was performed using Merck Silica gel GF. Solvents were purified using standard methods. All temperatures are Celsius unless otherwise indicated. The following abbreviations are employed: BSA—bovine serum albumin; BGG—bovine gamma-globulin; G6PDH—glucose-6-phosphate dehydrogenase; G6P—glucose-6-phosphate disodium salt; and DMF—dimethylformamide; AED - 0.55M Tris-HCl, pH 8.1; AND—nicotinamide adenine dinucleotide; NADP—nicotinamide adenine dinucleotide phosphate; DTE—dithioerythritol; and BAG - N-bromoacetyl glycine.

1. Preparation of 5-Formylsalicylic Acid (1)

5-Formylsalicylic acid ("hapten") is available from Aldrich. The hapten is purified by one methanol/water recrystallization before conjugation. Before conjugation, the hapten is dried overnight under vacuum at room temperature.

2. Conjugation of 5-Formylsalicylic Acid to BSA

The BSA (600mg; 9.3 $\mu$mol; 0.53 $\mu$mol of amine) was taken up into phosphate buffer (0.020M, pH 7) and the pH adjusted to 7.4. The solution was cooled to 0° C. and compound 1 (72mg; 0.43 mmoles) added and the pH adjusted to 7.4. The solution was stirred for 15 minutes, then NaBH$_3$CN (54mg; 0.86 mmoles) was added and the solution stirred overnight. The protein was then dialyzed (pH 8-9, NH$_4$OH) and concentrated. This procedure was repeated twice more. Dialysis and then Sephadex G-50 column with lyophilization afforded the conjugate with a hapten number of 10. This was determined by comparison of a mechanical mixture of salicylic acid and BSA with the conjugate.

3. Conjugation of 5-Formylsalicylic Acid to BGG

The BGG (600mg; 3.4 μmoles, $3.08 \times 10^{-4}$ moles of amine) was taken up into phosphate buffer (0.020M; pH 7.2) and the pH adjusted to 7.4. The solution was cooled to 0° C. and compound 1 (51mg; 0.308 mmoles) was added, the pH adjusted to 7.4 and the solution stirred for 15 minutes. Then NaBH$_3$CN (39mg; 0.616 mmoles) was added and the solution stirred for 3-4 hours. An additional amount of NaBH$_3$CN (39mg) was added and the solution stirred overnight. The protein was then dialyzed (pH 8-9, NH$_4$OH) and concentrated. The procedure was repeated. Dialysis followed by chromatographic separation on a Sephadex G-50 column yielded conjugate with a hapten number of 10. The hapten number was estimated by a mechanical mixture of salicylic acid with BGG.

4. Conjugation of 5-Formylsalicylic Acid to G6PDH

The following solutions are prepared:
(a) G6PDH Solution.

G6P is added to G6PDH (5mg/ml 0.05M bicine) to a concentration of 20mg G6P/mg G6PDH. The resulting solution is stored at 4° C. with stirring.

(b) Hapten Solution

Dried 5-formylsalicylic acid is weighed into a vessel in a dry (10% rel. humidity) room. The hapten is quickly dissolved in dry DMF to a final concentration of 0.5 μmole/μl at room temperature with stirring. The resulting solution is stored at 4° C. with stirring.

(c) NaBH$_3$CN

In a dry room, the NaBH$_3$CN is weighed into a container and cold 0.05 M bicine is added to it until the final concentration is 5 μmole/μl. The NaBH$_3$CN solution should be clear and colorless and dissolution should be almost instantaneous. The solution should be kept cold to minimize hydrolysis of the NaBH$_3$CN. The solution is prepared just before addition to the hapten.

The conjugation is performed as follows: Hapten solution and G6PDH solution are admixed using a Hamilton syringe at a rate of 100 μl hapten solution and 5 ml of G6PDH solution per minute. It is important that the rate not be exceeded and that the hapten solution be kept at 4° C. After additions are completed, the hapten solution and G6PDH solution should be allowed to incubate for 15-20 minutes.

The NaBH$_3$CN is then added. Additions must be done slowly to avoid high localized concentration of borohydride. It should also be done expeditiously to minimize decomposition of the borohydride prior to addition to the hapten/enzyme mixture. The addition was accomplished at 50 μl NaBH$_3$CN per 5 mls of hapten/G6PDH mixture per minute.

After the NaBH$_3$CN is added, the reaction mixture should be kept at 4° C., with stirring, in the dark until either the predetermined endpoints are reached or more NaBH$_3$CN needs to be added in order to speed up the rate of labeling. Further NaBH$_3$CN additions are done in the same manner and at the same ratio, always 2:1 NaBH$_3$CN:hapten.

After the 40-60% deactivation with 50-70% inhibition endpoints are achieved, cleanup of the conjugate is done immediately to avoid further deactivation and labeling. Cleanup involves Sephadex G50 column chromatography at a sample to bed volume ratio of >1:20. The eluent is AED and the flow rate is at >1 ml/minute.

A single chromatographic cleanup, thus far appears sufficient. All conjugates checked for any free hapten soon after cleanup have been negative. Additional hydroxylamine treatment showed no improvement in conjugate performance.

5. Cross-Reactivity

Referring to Table 1, the cross-reactivity of the antibodies of the present invention was checked against other drugs. A sheep was immunized with antigen according to Example 3. The antisera produced at the O bleed was used in comparative assays employing G6PDH conjugate prepared according to Example 4.

The following reagents were employed:
Enzyme diluent: 0.055M Tris-buffer; 1.0% RSA; 0.9% NaCl; 0.32M G6P; 0.05% sodium azide; 0.005% Thimerosal; 5, conc. HCl to bring to pH 6.2.

Antibody diluent: 0.05M Tris-buffer, pH 8.1; 0.005% Thimerosal; 0.05% sodium azide; 0.066M G6P; 1.0% RSA; 0.04M AND.

Assay buffer: 0.055M Tris-buffer; 0.005% Themerosal; 0.05% sodium azide; 0.5% NaCl; 0.01% Triton X-100; conc. HCl to bring to pH 8.1.

The enzyme reagent employs sufficient enzyme conjugate (according to Example 4) in enzyme diluent such that the maximum rate does not exceed 50 OD units. In carrying out the assay, a Gilford 300N micro-sample spectrophotometer with a thermocuvette was employed.

The protocol of the assay is as follows: 50μl of the sample is drawn up into a diluter-pipetter and dispensed with 250μl of the assay buffer into a 1 ml Croan cup, followed by addition of 50μl of the antibody reagent (antibody in antibody diluent optimized for assay), 250μl of assay buffer, followed by 50 μl of the enzyme reagent and 250μl of assay buffer. Immediately after the enzyme addition, the entire sample is aspirated into the flow cell. After 15 sec. a first reading is taken, followed by a second reading after a 30-sec. interval. The results compared in Table 1 are the difference in absorbance reported for each of the drugs tested.

TABLE 1

| | Drug | Maximum Concentration Tested | Concentration of Compound Equivalent to 2.5 mg/dl Salicylic acid | Percent Interference at 2.5 mg/dl Salicylic acid |
|---|---|---|---|---|
| 1. Precursor: | acetylsalicylic acid | 50 mg/dl | 3.3 mg/dl | 75% |
| 2. Metabolites: | salicyluric acid | 100 mg/dl | | 0% |
| | gentisic acid | 100 mg/dl | 4.5 mg/dl | 55% |
| | 2,3-dihydroxybenzoic acid | 100 mg/dl | 44 mg/dl | 6% |
| 3. Concurrently given drugs: | acetaminophen | 50 mg/dl | | 0% |
| | salicylamide | 50 mg/dl | | 0% |
| | dextromethorphan | 100 mg/dl | | 0% |

TABLE 1-continued

| | Drug | Maximum Concentration Tested | Concentration of Compound Equivalent to 2.5 mg/dl Salicylic acid | Percent Interference at 2.5 mg/dl Salicylic acid |
|---|---|---|---|---|
| | codeine | 100 mg/dl | | 0% |
| 4. Structurally similar compounds: | methyl salicylate | 50 mg/dl | 15 mg/dl | 17% |
| | phenylephrine | 50 mg/dl | | 0% |
| 5. Other drugs: | caffeine | 100 mg/dl | | 0% |
| | naloxone | 100 mg/dl | | 0% |
| | propoxyphene | 100 mg/dl | | 0% |
| | secobarbital | 100 mg/dl | | 0% |
| | amphetamine | 100 mg/dl | | 0% |
| | cocaine | 100 mg/dl | | 0% |
| | atropine | 100 mg/dl | | 0% |
| | naproxen | 100 mg/dl | | 0% |

The results show that methyl salicylate, acetylsalicylic acid, gentisic acid and 2,3-dihydroxybenzoic acid are the only potential cross-reactants. The percent of cross-reactivity was calculated using direct equivalence for the analyte.

These cross-reactivities should not interfere with the assay. Acetylsalicylic acid is the direct precursor of salicylic acid which is rapidly deacetylated in vivo. Gentisic acid and 1,3-dihydroxybenzoic acid are reported to be less than 1% of the metabolic product of salicylate therapy, and would be present in non-interfering amounts in serum. Methyl salicylate (oil of wintergreen) is present at low concentration in some candies.

6. 5-(S-Methyldithioglycolamido;-2-hydroxybenzoic acid (3)

The ester N-succinimidyl methyldithioglycolate 2 (1.065g, 4.53mmol 1.13 equivalent) in THF (6ml) was added dropwise to the amine 5-aminosalicylic acid 4 (612mg, 4.0mmol) in THF/carbonate buffer (1:1, pH 9.5; 14ml volume) and stirred for 3 hours. The solution was acidified and extracted with ether. The combined extracts were washed with brine, dried (MgSO4), filtered, and concentrated. Recrystallization (hexane/acetone) gave pure 3, m.p. 202–207° C. (dec.).

7. Preparation of the BSA conjugate of S-(3-carboxy-4-hydroxyanelinocarbonylmethyl) N'-mercaptoacetyl glycine The disulfide 3 (218 mg, 0.80 mmole) and DTE (123 mg; 0.80 mmole) were taken up into CH3H (20 ml deoxygenated) and treated with Et3N (160 μl, 1.2 mmol) in the cold for 26 hours under N2. The solution was concentrated in vacuo and immediately taken up into CH3OH (10 ml) to give a 0.08 mmole/mL solution of the thiol.

Then the thiol (8 ml) was added to a solution of bromoacetylglycylglycine substituted BSA (BAG-BSA) (prepared from 0.1 mmol of BSA) in water and the pH adjusted to 7. The solution was allowed to stir for 24 hours keeping the pH at about 7. The solution was concentrated using an Amicon filter to 50 ml and then chromatographed on G-50, (H2O) and lyophilized. This gave a hapten number of approximately 10. The hapten number was determined by comparison with a mechanical mixture of N-acetyl 4 and BSA with the conjugate.

8. Trans-3'-Carboxy-4'-hydroxycinnamic acid (5)

5-Formylsalicylic acid (1.66 g, 10 mmol) and malonic acid (2.08 g, 20 mmol) were heated in pyridine (10 ml) with piperidine (0.5 ml) at 100° C. for 4 hours. The solution was acidified and the solid collected and washed with water. Recrystallization from acetone/water afforded the pure diacid 5.

9. 3-(3'-Carboxy-4'-hydroxyphenyl)propionic acid (6)

The diacid 5 (792 mg, 3.80 mmol) was taken into absolute ethanol and hydrogenated with 45 psi of H2 and PtO2 (34 mg) for 4 hours. The solution was filtered over celite and concentrated in vacuo to afford 741 mg (93%) of 6.

10. Ethyl, trans-3'-carboxy-4'-hydroxycinnamoate (7)

5-Formylsalicylic acid (3.32 g, 20 mmole) and ethyl acetate (20.8 g, 60 mmole) were heated to 50° C., under nitrogen, in THF (100 ml) overnight. The solution was cooled, ether added (200 ml) and acidified with 1 N HCl. The organic layer was removed and the aqueous layer extracted with ether. The combined ethereal extracts were washed with brine (100 ml), dried (MgSO4), filtered, and concentrated. Chromatography (hexane/ethylacetate/HOAc, 1:1:1%) gave 2.10 g (44%) of 7.

11 Ethyl 3-(3'-carboxy-4'-hydroxyphenyl)propanoate acid (8)

The ester 7 (2.10g, 8.82mmol) was taken up into absolute ethanol (50ml) and hydrogenated at 45 psi of H2 over PtO2 (100mg) overnight. The solution was filtered over a celite pad and concentrated in vacuo to give 2.05g (97%) of 8. Recrystallization from hexane/ethylacetate gave pure 8.

12. 5-(3'-Hydroxypropyl)-2'-hydroxybenzoic acid (9)

The ester 8 (2.05 g, 8.62 mmol) in THF (50 ml) was added dropwise to an ice-cold suspension of LiAlH4 (818mg, 21.5mmol, 2.5 equivalent) in THF (50ml) and the solution stirred for 1 hour. Water was carefully added and then the solution acidified with 1N HCl and extracted with ether. The combined ethereal extracts were washed with brine, dried (MgSO4), filtered, and concentrated in vacuo. Recrystallization (hexane/acetone) gave 1.28g (76%) of 9, m.p. 128–130° C.

13. 5-(3'-Bromopropyl)-2-hydroxybenzoic acid (10)

The alcohol 9 (1.39g, 7.09mmol) was taken up into 48% HBr(15ml) and heated at 100° C. for 1.5 hours. The solution was cooled and extracted with ether (4×50ml). The combined extracts were washed with brine (50ml), dried (MgSO4), filtered, and concentrated in vacuo to give 1,6g (87%) of crude bromide.

14. 5-(3'-Thioacetylpropyl)-2-hydroxybenzoic acid (11)

The bromide 10 (1.6g; 6.17mmol) was taken up into methanol/water (25ml/1ml) and treated with thioacetic acid (1.32ml; 1.40g, 18.5mmol, 3 equivalents) and $K_2CO_3$(2.25g, 18.5mmol, 3 equivalents) at room temperature for 20 hours. The solution was acidified with 1N HCl and extracted with ether. The combined ether extracts were washed with brine, dried ($MgSO_4$), filtered and concentrated. Radial chromatography (hexane/ethylacetate HOAc, 1:1:1%) gave 1.125g (72%) of 10, m.p. 68-73° C.

15. Preparation of S-(3-[3'-carboxy-4'-hydroxyphenyl]propyl) N-mercaptoacetyl glycine conjugate of BSA Activation of hapten: The thiolacetate 11 (290mg, 1.1mmol) in $CH_3OH$ (11ml; deoxygenated) was refluxed with $K_2CO_3$(2.2eq.; 2.42mmol; 346mg) for 0.5 hours under $N_2$. This solution of the mercaptan 12 was used immediately as below.

Conjugation Procedure: To BSA (644mg; 0.01mmol; 0.6mmol of amine) in borate buffer (0.1 M; 30 ml; pH 8.0) was added the NHS ester of bromoacetyl glycine (BAG-NHS) (293mg; 1.0mmol; 1.6:1 NHS:$NH_2$) in DMF (1ml) at 0° C. with stirring. The pH was maintained between 7.5 and 8.0 during the addition (20min) and then brought below pH 7 for 3 hours. The solution was chromatographed on Sephadex G-50 ($H_2O$) and the protein fractions collected and stored overnight. This solution was reacted with 6ml of the above prepared solution of the thiol in the cold for 36 hours. The solution was concentrated via an Amicon filter (PM 10) to about 30ml in volume. This solution was chromatographed on Sephadex G-50 ($H_2O$, pH 7-8) and protein fractions collected. This afforded ~500mg of protein material with a hapten number of 10.

The hapten number was determined via comparison of a mechanical mixture of 5-methylsalicylic acid and BSA with the conjugate at λ305.

16. Preparation of the conjugate of BGG Activation of

Hapten: This procedure was the same as for the conjugation with BSA.

Conjugation Procedure: The procedure was the same as for the BSA conjugation except the following amounts were used: BGG (650mg; 3.7μmol; 0.334mmol of amine); BAG-NHS (163mg; 0.557mmol; 1.6:1 NHS:amine); borate buffer (30ml, pH 8.0; 0.1M); thiol solution (4ml; 0.4mmol).

The resulting solution was concentrated via an Amicon filter (PM 10) to approximately 30ml in volume. This was chromatographed on Sephadex G-50 ($H_2O$) and protein fractions collected to produce 665mg of material. This had a hapten number of 14 as determined by a mechanical mixture of 5-methylsalicylic acid and BGG with the conjugate at λ305.

17. Preparation of conjugate of (3) with G6PDH

To a solution of G6PDH at 5mg/ml in 55mM Tris was added G6P monosodium salt and NADH at a ratio of 20 mg/mg enzyme. pH at 4° is 8.5-9.0. BAG-NHS was dissolved in dried DMF. While maintaining a 4° temperature, argon was bubbled through the solution for 30 min. The BAG-NHS solution was slowly added to the enzyme solution (0.1 mg BAG-NHS/min.). Additions were continued until the enzyme was 60-65% deactivated. The G6PDH-BAG-NHS solution was then dialyzed against 55mM Tris pH 7.0 overnight at a ratio of 1:1000. The buffer was changed 3 times.

To the salicylic acid disulfide (3) was added DTE triethylamine at a molar ratio of 1:1:1.1. The entire solution was diluted with dried DMF to a final disulfide concentration of 0.2M. The solution was adjusted to pH 10 and argon was bubbled through the solution for 1.5 hours. The pH was then adjusted to 7. Argon was again bubbled through 3-5 minutes. The solution was capped and left stirring at 4° overnight.

The BAG-G6PDH solution was adjusted to pH 8.5 and argon was bubbled through the solution for one hour. The reduced salicylic acid disulfide 3 solution prepared above was added slowly (2μmoles/min.) until the conjugate was 60% inhibitable and 74% deactivated using antisera raised against the disulfide derivative. The conjugate was then chromatographed using Sephadex G-50 with 55mM Tris +0.05% azide and 0.005% thimerosal as the eluate.

Following the procedure described previously, antibodies obtained in response to the immunogens were employed in an immunoassay for salicylic acid and their dynamic range determined. That is, the number of units expressed as optical density units which are measured between a sample having no salicylic acid and a sample having 1mg/ml.

TABLE 2

| | Data Showing Usefulness of Antibodies* | | | |
|---|---|---|---|---|
| | | % Inhibition | | |
| Immunogen | Sheep # | Maximum | Used for Modulation | Separation, ΔOD Neg-1000 μg/ml |
| Ex. 16 | 3355 | 75 | 13 | 130 |
| | 3356 | 76 | 41 | 70 |
| | 3357 | 53 | 30 | 180 |
| | 3358 | — | 21 | 145 |
| Ex. 16 | 3595 | 72 | 48 | 70 |
| | 3596 | 67 | 32 | 80 |
| Ex. 15 | 3362 | 80 | 41 | 80 |

*Enzyme conjugate used is Example 17

The compositions of the subject invention provide for reagents which allow a sensitive, accurate assay for salicylate in patient serum samples. The antigenic conjugates provide for the efficient production of antibodies having high affinity and high titer for salicylate. The combination of these antibodies and the enzyme conjugates allows the accurate, rapid assay for salicylate.

Although the foregoing invention has been described in some detail, by way of illustration and example for purposes of clarity and understanding, it will be obvious that certain changes and modifications may be practiced within the scope of the claims.

What is claimed is:

1. A compound of the formula:

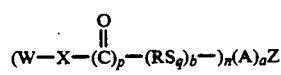

wherein:

W is 3-carboxy-4-hydroxyphenyl-1;
X is a bond or —NH—;
p is 0 or 1, being 1 when X is NH;
R is alkylene of from 1 to 6 carbon atoms;
S is sulphur;
b and q are 0 or 1;
Z is a poly(amino acid) and said poly(amino acid) is an enzyme;

n is a number from 1 to the molecular weight of said enzyme divided by 500;

a is 0 up to n, being 0 when q is 0; and

A is derived from a functionality capable of reacting with a thiol group.

2. A compound according to claim 1, wherein said enzyme is glucose-6-phosphate dehydrogenase.

3. A method for determination of salicylates in a biological specimen, said method comprising:

combining (1) antibodies prepared in response to an antigen which is a compound of the formula:

$$(W-X(C)_p-(RS_q)_b)_n(A)_a Z$$

wherein:

W is 3-carboxy-4-hydroxyphenyl-1;

X is a bond or —NH—;

p is 0 or 1, being 1 when X is NH;

R is alkylene of from 1 to 6 carbon atoms;

S is sulphur;

b and q are 0 or 1;

Z is a poly(amino acid);

n is a number from 1 to the molecular weight of said enzyme divided by 500;

a is 0 up to n, being 0 when q is 0; and

A is derived from a functionality capable of reacting with a thiol group, (2) an enzyme-salicylate conjugate, (3) substrate for the enzyme, and (4) the biological specimen in an aqueous, buffered medium; and observing the rate at which the substrate is converted to product, which rate is related to the amount of salicylate in the specimen.

4. A method as in claim 3, wherein the enzyme is glucose-6-phosphate dehydrogenase and the substrate is AND or NADP.

5. A method for the determination of salicylates in a biological specimen, said method comprising;

combining an enzyme conjugate according to claim 1, enzyme substrate, antibody to salicylate, and the biological specimen in an aqueous, buffered medium; and observing the rate at which the substrate is converted to product, which rate is related to the amount of salicylate in the specimen.

6. A method as in claim 5, wherein the enzyme is glucose-6-phosphate dehydrogenase and the substrate is AND or NADP.

* * * * *